United States Patent [19]
Rudischhauser et al.

[11] Patent Number: 6,077,220
[45] Date of Patent: Jun. 20, 2000

[54] ENDOSCOPE WITH DRYING AGENT

[75] Inventors: Jürgen Rudischhauser; Siegfried Höfig, both of Tuttlingen, Germany

[73] Assignee: Karl Storz GmbH & Co. KG, Germany

[21] Appl. No.: 09/230,554

[22] PCT Filed: Jul. 29, 1997

[86] PCT No.: PCT/DE97/01603

§ 371 Date: Jan. 28, 1999

§ 102(e) Date: Jan. 28, 1999

[87] PCT Pub. No.: WO98/04947

PCT Pub. Date: Feb. 5, 1998

[30] Foreign Application Priority Data

Jul. 29, 1996 [DE] Germany ................ 196 30 634
Nov. 19, 1996 [DE] Germany ................ 196 47 851

[51] Int. Cl.⁷ ........................................ A61B 1/06
[52] U.S. Cl. ............................. 600/162; 359/513
[58] Field of Search ........................ 600/160, 162, 600/176; 359/811, 819, 513, 514

[56] References Cited

U.S. PATENT DOCUMENTS

| | | | |
|---|---|---|---|
| 2,399,971 | 5/1946 | Wolfe | 359/512 |
| 4,755,031 | 7/1988 | Daviau et al. | 359/512 |
| 5,836,867 | 11/1998 | Speier et al. | 600/112 |
| 5,839,284 | 11/1998 | Wyatt et al. | 62/3.2 |
| 5,868,664 | 2/1999 | Speier et al. | 600/112 |

*Primary Examiner*—Linda C. M. Dvorak
*Assistant Examiner*—Brad C. Blaise
*Attorney, Agent, or Firm*—St. Onge Steward Johnston & Reens LLC

[57] ABSTRACT

What is described here is an endoscope including an endoscope optical system and a desiccant which is introduced into and fixed in the mounting space of the endoscope optical system. The invention excels itself by the provisions that the desiccant is present in the form of a plurality of spheres (5) and/or rod-shaped elements which are inserted into at least one recess (4) in the mounting space, and fixed by means of at least one fixing element which contacts the spheres or the rod-shaped elements merely over part of their surface.

18 Claims, 1 Drawing Sheet

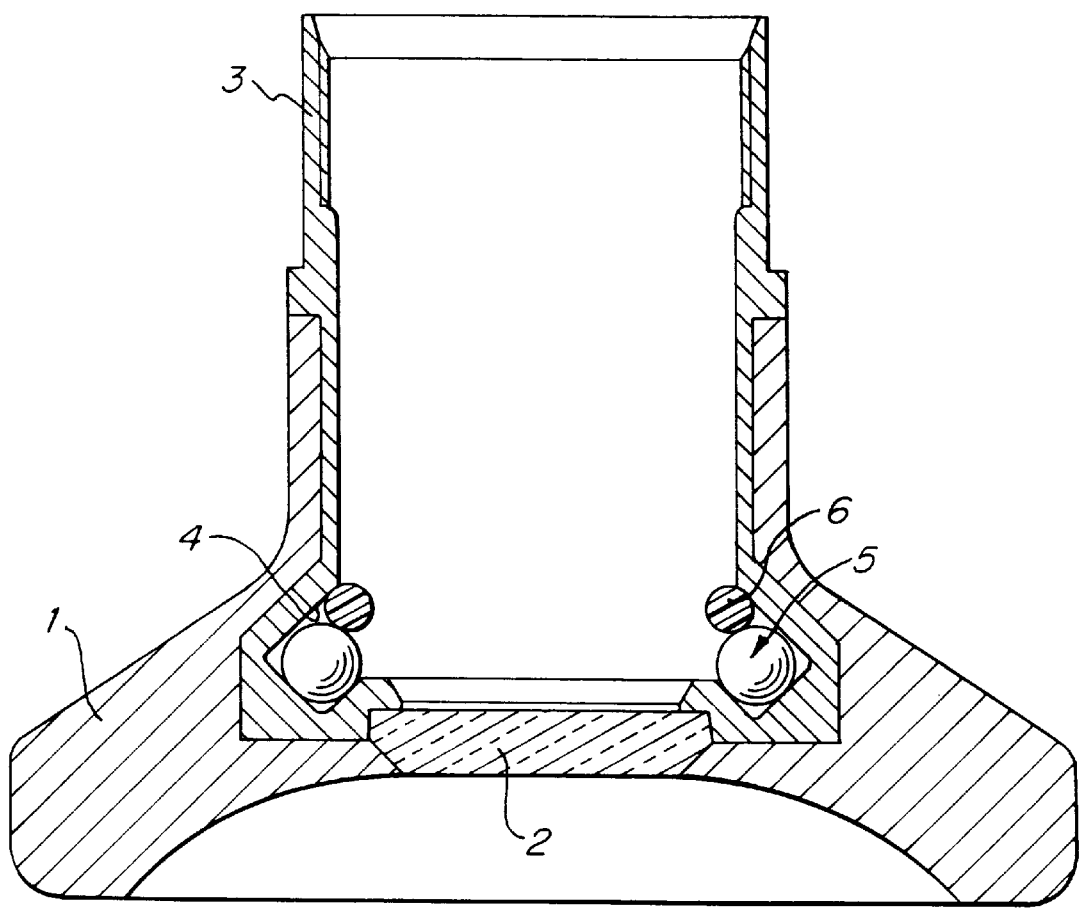

ENDOSCOPE WITH DRYING AGENT

DESCRIPTION

1. Field of the Invention

The invention relates to an endoscope with an endoscope optical system and a desiccant introduced into and fixed in the mounting space of the endoscope optical system.

2. Prior Art

Endoscopes and particularly endoscopes employed in biomedical engineering are fundamentally fluid-tight systems. For a number of reasons, however, moisture may occur in the mounting space of the optical system of the endoscope:

First, it is possible that due to the humidity of the air in the space where the endoscope is assembled some residual moisture remains in the mounting space of the endoscope. And secondly moisture may penetrate into the mounting space through slight leaks at joints, which, actually speaking, do not require an expensive repair of the endoscope.

For this reason it has been common for a major period of time already to provide a desiccant in the mounting space of the endoscope optical system for adsorption of this residual moisture.

Different solutions have become known for the incorporation of the desiccant into the mounting space of the endoscope optical system:

One example is the provision of the desiccant in bulk form in the mounting space. This approach presents the disadvantage, however, that noise will occur when the optical system is moved and that moreover dust may be produced as a result of desiccant abrasion caused by movement. The dust may deposit on the optical elements.

The German Patent DE 37 08 124 C2 discloses an endoscope with a hydroscopic element wherein the hydroscopic element is designed as flexible strip material and mounted in a part of the endoscope optical system between the lens carrier and the outer wall, which part is specifically provided to this end. That known endoscope, which the introductory clause of patent claim 1 starts out from, presents the disadvantage that an exchange of the hydroscopic element is possible only upon complete disassembly of the endoscope.

The German Patent DE 195 07 205 A1 has therefore proposed the provision of a hydroscopic substance underneath a removal wall element of he housing, which is connected to the remaining parts of the housing wall in a gas-tight manner by means of a coupler. This design presents the disadvantage that the endoscope has an opening wider than that which must be ensured to be fluid-tight.

BRIEF DESCRIPTION OF THE INVENTION

The present invention is based on the problem of improving an endoscope with an endoscope optical system and a desiccant which is introduced into and fixed in the mounting space of the endoscope optical system, in a way that the desiccant will be reliably fixed in the mounting space and has a high moisture adsorption efficiency so that an exchange of the desiccant is not required as a rule.

In accordance with the present invention the desiccant is present in the form of a plurality of spheres and/or rod-like elements which are inserted into at least one recess in the mounting space and which are fixed by means of at least one fixing element contacting the spheres or the rod-shaped elements merely over one part of their surface.

With this design the invention starts out from the finding that endoscopes must be suitable for disassembly for servicing reasons so that it is not necessary to provide an additional opening for the exchange of the desiccant.

On account of the fixed mounting of the desiccant in the mounting space of the optical system it is not necessary for an exchange of the desiccant to disassembly the endoscope beyond the measure common for regular servicing. Due to the provision of the desiccant in the zone of the eyepiece sufficient space is available for accommodating such an amount of desiccant that the desiccant quantity will be sufficient for an average service life of an endoscope. The desiccant may, of course, yet be exchanged whenever this will be necessary.

The use of a plurality of spheres and/or rod-shaped elements with a preferably cylindrical shape a large desiccant surface is achieved so that a high efficiency in desiccant adsorption will be reached.

The fixing element serves the purpose of first reliably fixing the desiccant, which is present in the form of spheres or rods of preferably cylindrical shape, and of secondly ensuring an unobstructed exchange of air so that the desiccant may adsorb any moisture present in the space where the optical system is mounted.

One advantage of the design is the major part of the desiccant surface free so that the moisture can be absorbed without any problems. Moreover, the O-rings may be replaced without any problems when the desiccant is exchanged.

The use of a container having a wall permeable to moisture and consisting particularly of a diaphragm ensures a reliable fixing even in the event of vibrations etc.

Various possibilities exist for the desiccant such as silica gel or porous ceramic material. Such desiccants, which may produce the effects of a molecular sieve in particular, are commercially available.

In an expedient improvement moisture-measuring means may be provided in the space where the optical system is mounted. Based on the result of measurement, the operator is able to determine whether the moisture in the mounting space of the optical system is within the range of acceptable limits. If an excessively high moisture is indicated this situation may be due to an exhaustion of the desiccant so that the latter must be exchanged, or whether the endoscope presents a leak through which moisture enters to an extent so high that it can no longer be adsorbed by the desiccant.

The moisture-measuring means can preferably include a chromatic indicator wherein the colour changes reversibly or irreversibly at a defined moisture lever and which is visible in a window from the outside. Such colour indicators are commercially available.

BRIEF DESCRIPTION OF THE DRAWING

The following is an exemplary description of the invention with reference to an embodiment, without any restriction of the general inventive idea, with the single FIGURE of the drawing being referred to which shows:

a cross-sectional view taken through the proximal part of an inventive endoscope

DESCRIPTION OF AN EMBODIMENT

The proximal part of an inventive endoscope, which is illustrated in the FIGURE, comprises a flaring eyepiece mount 1 with an eyepiece covering glass 2. The flaring eyepiece mount 1 is connected to a base part 3 of the endoscope in a manner known per se, which part is illustrated only partly. On the base part 3 the connector for a light guide is provided, for instance, which is not illustrated here.

Within the area of the eyepiece covering glass 2 a peripheral groove 4 is provided on the base part 3 in accordance with the invention, into which the desiccant spheres 5 are inserted. These spheres 5 are retained by an O-ring in order to prevent them from dropping out of the groove 4 due to movements of the endoscope.

This arrangements presents a number of advantages:
the desiccant spheres 5 present a comparatively large surface available for adsorption;
the surface is "freely accessible" since the O-ring contacts the spheres only over a comparatively small surface;
retrofitting of existing endoscopes to achieve the inventive embodiment is easily possible—by a replacement of the comparatively inexpensive proximal part or by subsequent provision of the groove 4;
the inventive arrangement of the desiccant does not require an enlargement of the dimensions of the endoscope; and yet vignetting of the optical path for observation does not occur.

The moisture-measuring means, which is provided in a preferred embodiment of the invention and which is not illustrated in the FIGURE, may equally be provided in the base part 3. The window for observation of the result of measurement and particularly for observation of the colour indicator whose colour undergoes a reversible or irreversible change at a defined moisture level, must, of course, be so disposed that light will not enter into the optical path for observation, which would produce the effects of interfering stray light.

What is claimed is:

1. Endoscope comprising an endoscope optical system and a desiccant introduced into and fixed in a mounting space of the endoscope optical system, characterized in that said desiccant is present in the form a plurality of spheres which are inserted into at least one recess in said mounting space and which are fixed by at least one fixing element which contacts said spheres over only a portion of their surface.

2. Endoscope according to claim 1, characterized in that said at least one fixing element is an O-ring (6) which fixes said desiccant in said recess.

3. Endoscope according to claim 1, characterized in that said at least one fixing element is a container having a wall permeable to moisture.

4. Endoscope according to claim 3, characterized in that the wall of said container consists of a diaphragm.

5. Endoscope according to claim 1, characterized in that said endoscope includes a flaring eyepiece mount, and in that said desiccant is arranged adjacent of the flaring eyepiece mount (1).

6. Endoscope according to claim 1, characterized in that said desiccant is a silica gel or a porous ceramic material.

7. Endoscope according to claim 1, characterized in that a moisture-measuring means is provided in the space where the optical system is mounted.

8. Endoscope according to claim 7, characterized in that said moisture-measuring means comprises a colour indicator whose colour undergoes a reversible or irreversible change at a defined moisture level, and is visible in a window from the outside.

9. Endoscope according to claim 1, characterized in that said fixing element is so configured that said desiccant may be exchanged in the course of regular endoscope servicing.

10. Endoscope comprising an endoscope optical system and a desiccant introduced into and fixed in a mounting space of the endoscope optical system, characterized in that said desiccant is present in the form a plurality of rod-shaped elements which are inserted into at least one recess in said mounting space and which are fixed by at least one fixing element which contacts said rod-shaped elements over only a portion of their surface.

11. Endoscope according to claim 10, characterized in that said at least one fixing element is an O-ring (6) which fixes said desiccant in said recess.

12. Endoscope according to claim 10, characterized in that said at least one fixing element is a container having a wall permeable to moisture.

13. Endoscope according to claim 12, characterized in that the wall of said container consists of a diaphragm.

14. Endoscope according to claim 10, characterized in that said endoscope includes a flaring eyepiece mount, and in that said desiccant is arranged adjacent the flaring eyepiece mount (1).

15. Endoscope according to claim 10, characterized in that said desiccant is a silica gel or a porous ceramic material.

16. Endoscope according to claim 10, characterized in that a moisture-measuring means is provided in the space where the optical system is mounted.

17. Endoscope according to claim 16, characterized in that said moisture-measuring means comprises a color indicator whose color undergoes a reversible or irreversible change at a defined moisture level, and is visible in a window from the outside.

18. Endoscope according to claim 10, characterized in that said fixing element is so configured that said desiccant may be exchanged in the course of regular endoscope servicing.

* * * * *